United States Patent [19]
Munsinger et al.

[11] Patent Number: 6,042,588
[45] Date of Patent: Mar. 28, 2000

[54] STENT DELIVERY SYSTEM

[75] Inventors: Joel R. Munsinger, Albertville; Jon St. Germain, Elk River, both of Minn.

[73] Assignee: Scimed Life Systems, Inc, Maple Grove, Minn.

[21] Appl. No.: 09/033,724

[22] Filed: Mar. 3, 1998

[51] Int. Cl.[7] .................................................. A61F 11/00
[52] U.S. Cl. ............................................................ 606/108
[58] Field of Search .................................... 606/108, 194, 606/184; 604/171, 158, 264, 280

[56] References Cited

U.S. PATENT DOCUMENTS

| | | | |
|---|---|---|---|
| 5,360,401 | 11/1994 | Turnland | 604/96 |
| 5,441,516 | 8/1995 | Wang et al. | 606/198 |
| 5,480,383 | 1/1996 | Bagaoisan et al. | 604/96 |
| 5,499,973 | 3/1996 | Saab | 604/96 |
| 5,534,007 | 7/1996 | S.t Germain et al. | 606/108 |
| 5,545,138 | 8/1996 | Fugoso et al. | 604/102 |
| 5,549,552 | 8/1996 | Peters et al. | 604/96 |
| 5,554,121 | 9/1996 | Ainsworth et al. | 606/198 |
| 5,571,135 | 11/1996 | Fraser et al. | 606/198 |
| 5,605,543 | 2/1997 | Swanson | 604/96 |
| 5,632,760 | 5/1997 | Sheiban et al. | 606/191 |
| 5,772,669 | 6/1998 | Vrba | 606/108 |
| 5,776,140 | 7/1998 | Cottone | 606/108 |
| 5,776,141 | 7/1998 | Klein et al. | 606/108 |

*Primary Examiner*—Michael Buiz
*Attorney, Agent, or Firm*—Vidas, Arrett & Steinkraus, P.A.

[57] ABSTRACT

A stent delivery catheter comprising a stiff proximal shaft, a manifold, a distal shaft, a pull back stent release assembly and a pull back wire and a guide wire, both extending through the catheter from the manifold to the distal end of the catheter. The proximal shaft encloses a pull back wire shaft and a guide wire shaft. The proximal shaft may be made of an extruded polymer having two lumens disposed therein to receive the separate wires, keeping them separate.

24 Claims, 3 Drawing Sheets

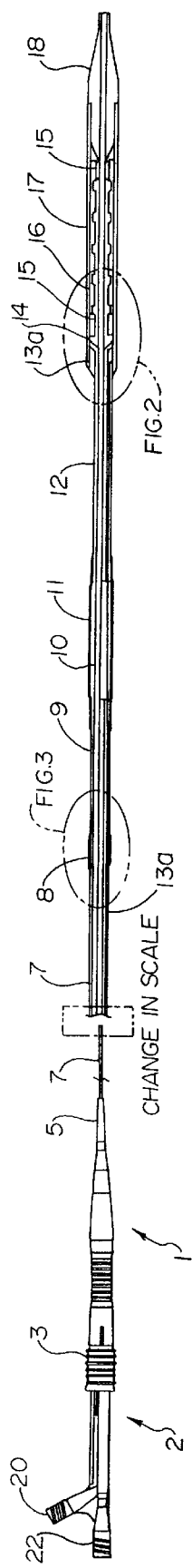
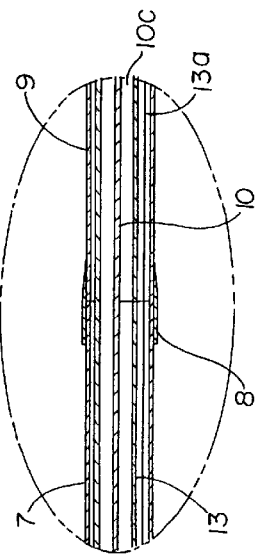
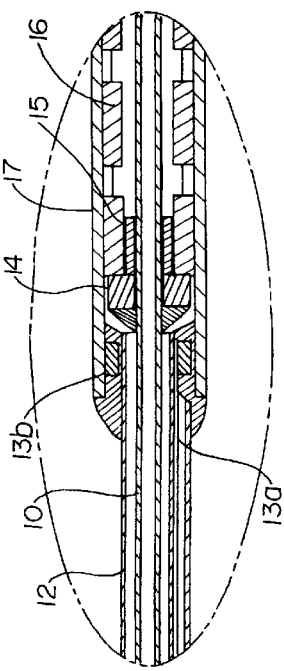

STENT DELIVERY SYSTEM

FIELD OF THE INVENTION

The present invention relates to an improved delivery system for delivering and deploying a medical device, such as a stent, used in percutaneous transluminal coronary angioplasty (PTCA) procedures. More specifically, the invention relates to a stent pull back delivery system having a stiffer proximal shaft housing multiple lumens for more accurate placement of the medical device.

BACKGROUND OF THE INVENTION

In typical PTCA procedures, a guiding catheter is percutaneously introduced into the cardiovascular system of a patient and advanced through the aorta until the distal end is in the ostium of the desired coronary artery. Using fluoroscopy, a guide wire is then advanced through the guiding catheter and across the site to be treated in the coronary artery. An over the wire (OTW) catheter is advanced over the guide wire to the treatment site. The medical device is then expanded to reopen the artery. The OTW catheter may have a guide wire lumen which is as long as the catheter or it may be a rapid exchange catheter wherein the guide wire lumen is substantially shorter than the catheter and enters the catheter at the distal portion. Alternatively, a fixed wire balloon may be used. This device features a guide wire which is affixed to the catheter and cannot be removed. Such procedures and catheters are well known.

To help prevent arterial closure, repair dissection, or prevent restenosis, a physician can implant an intravascular prosthesis, or a stent, for maintaining vascular patency inside the artery at the lesion. The stent may either be a self-expanding stent or a balloon expandable stent. For the latter type, the stent is often delivered on a balloon and the balloon is used to expand the stent. The self-expanding stents may be made of shape memory materials such as nitinol or constructed of regular metals but of a design which exhibits self expansion characteristics.

In certain known stent delivery catheters, a stent and an optional balloon are positioned at the distal end of the catheter, around a core lumen. The stent and balloon are held down and covered by a sheath or sleeve. When the distal portion is in its desired location of the targeted vessel the sheath or sleeve is pulled back to expose the stent. After the sheath is removed, the stent is free to expand or be expanded. In order to remove the retaining sheath which contains the stent, devices such as pull back means are utilized such that the physician may controllably retract the sleeve from the proximal end to release the medical device. Example of such catheters can be found in U.S. Pat. Nos. 5,534,007, 5,360,401 and 5,571,135, all of which are herein incorporated by reference in their entirety.

Dilation catheters generally have been recently made to have low profiles with stiffer proximal shafts while maintaining flexible distal shafts. A stiffened proximal shaft provides greater push to the catheter which facilitates advancement over a guidewire in the tortuous anatomy. It is also found to be important with stent delivery systems is to have an material which has as close to a one to one force ratio as possible such that the physician may accurately locate the stent within the target area with out any additional "play" in the catheter due to the flexibility of the overall shaft. Stiffened proximal shaft section formed of plastic materials, stainless steel and superelastic NiTi alloys are disclosed in the prior art. However, the raw material and manufacturing costs for a catheter having a relatively stiff proximal shaft is high. The present invention provides an intraluminal catheter which has a low profile and a relatively stiff proximal shaft which has an improved force ratio which is easy and inexpensive to manufacture.

A typical catheter utilizing pull back means has a proximal shaft housing a guidewire lumen and a free floating pull back wire with no separate track or lumen. A further problem found with stent delivery catheters utilizing a pull back means and a guide wire, as mentioned above, is that during manufacturing and/or the tortuous feeding of the catheter through the body, the pull back wire and the guide wire, and/or guide wire lumen, tend to get tangled with each other causing a recoiled spring phenomenon (scrunching or a choke collar type effect) in the catheter and/or a jumping forward of the distal end of the catheter when the retaining means is retracted to release the medical device. The present invention eliminates interaction between the wires and serves to solve this problem as well.

Related prior art of interest include U.S. Pat. Nos. 5,480,383, 5,549,552, 5,499,973, 5,545,138, 5,605,543 and 5,554,121, all of which are herein incorporated by reference in their entirety.

SUMMARY OF THE INVENTION

The present invention provides a novel construction of the proximal portion of any catheter utilized for stent delivery. More specifically, the inventive concept is preferably utilized with a stent delivery catheter, such as an Over the Wire (OTW) catheter, constructed to include a guide wire and optionally a guide wire shaft and a pull back wire which functions to pull back a distal sheath which retains a loaded self-expanding stent or a balloon expandable stent to release said stent into a prescribed area. Basically, the invention provides for a stiffer proximal shaft having multiple tracks/lumens/shafts for the separation of the guide wire lumen and the pull back wire.

Advantages of the present invention include trackability and push. Non-stent delivery systems depend on lower profiles and more flexibility to reach target lesions. However, with the addition of a stent, profiles are increased and flexibility is reduced, thus limiting the ability of the delivery system to reach its target lesion. A stiff proximal shaft compensates for the larger profiles and less flexible stent regions on loaded delivery systems. When the distal portion of a delivery system meets with resistance, the stiff proximal shaft becomes the backbone affording stiffness closer to the manifold and supports the device through the anatomy.

Device stability is also an important feature and is provided by the present invention. When the delivery system meets resistance a stiff proximal shaft would give the user a more "one-to-one" force response with advancement, where as a less stiff proximal shaft would coil up like a spring within the guide.

The present invention also provides deployment accuracy. When the delivery system gives the user a more one-to-one control it also enhances the users ability to correctly place the stent within the anatomy without the possibility of further complications due to the release of the above said coiled device as it reaches the force needed to advance and springs forward beyond the target lesion in addition to eliminating interaction between the wires, which can ordinarily entangle further causing jumping.

Accordingly, it is a general object of this invention to provide a stent deployment catheter apparatus having a proximal shaft characterized by increased stiffness and separate, multiple lumens for the guide wire and the pull back wire.

A principle object of this invention is to provide a relatively inexpensive and adaptable design for a multiple lumen stiff proximal shaft.

These and other objects and advantages of this invention will be better understood from the following description, which is to be read together with the accompanying drawings.

BRIEF DESCRIPTION OF THE FIGURES

FIG. 1 shows a side view of a catheter according to the invention having a loaded stent including a cross section view of the distal portion thereof and a side view of the proximal end of a catheter according to the invention showing the manifold portion thereof.

FIG. 2 shows a partial cross section of the distal portion of the catheter of FIG. 1.

FIG. 3 shows a partial cross section of the catheter of FIG. 1.

DETAILED DESCRIPTION OF THE INVENTION

Figure 4:
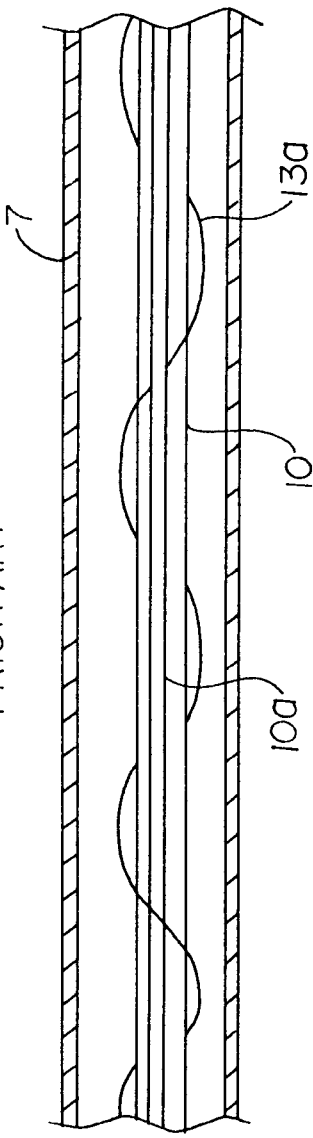
FIG. 4 shows a prior art partial cross section of a proximal shaft.

Proximal shaft construction in a stent delivery catheter is a critical feature that requires special consideration in order to have controlled insertion and accurate placement of the stent. A very stiff proximal shaft is a desirable feature for many reasons, including enhanced catheter push, deployment accuracy and one to one trackability. A number of shafts which fulfill these features are disclosed herein. This may be done by utilizing a proximal shaft with a braid reinforced guide wire shaft, supplemented with a pull back wire shaft. The braided guide wire lumen provides a superior strain relief mechanism as it transitions to the distal shaft segment. This allows a very stiff, compression resistant shaft that is still low profile.

An alternative to this desired shaft performance is the selection of a material that can be formed through extrusion into a solid shaft. Such a proximal shaft would be a solid one piece shaft having dual lumens formed within the shaft while maintaining a low profile. One extrusion of material having two lumens creates a stiffer shaft which is easier and cheaper to manufacture. This is preferably supplemented with an inner guide wire shaft disposed within one of the lumens.

The following descriptions of the invention are based on the delivery system of U.S. Pat. No. 5,534,007, which is herein incorporated by reference in its entirety, as an example of a stent delivery system utilizing a pull back means to release the stent. It should be understood that the present invention may be applied to any such stent delivery system.

FIG. 1 shows such a pull back stent delivery catheter, generally designated as 1. Generally, as a summary of U.S. Pat. No. 5,534,007, catheter 1 has a manifold 2 comprising a flush 20 and guide wire 22 access, a sheath actuator 3, which allows the user to retract the deployment sheath 17, and a strain relief portion 5. Extending distally, the manifold 2 is connected to the proximal shaft 7, which is the primary focus of the present invention, which is connected to the midshaft 9, preferably made of polyethylene. The midshaft is connected to the optional, but preferable, accordion shaft 11, which is in turn connected to the distal shaft 12. The distal portion, which is connected to the distal portion of the distal shaft, comprises the distal tip 18, the deployment sheath 17, the stent 16, marker bands 15 and a bumper 14. The combined shafts house a guide wire inner shaft 10, a guide wire 10a, a pull back wire lumen 13, pull collar 13b and a pull back wire 13a, which is connected to the deployment sheath 17 for release of the stent 16. Typically, a guide catheter covers the proximal shaft, which when inserted into the body follows a relatively linear path, but still must absorb the force built up from the more flexible distal portion carrying the more rigid stent portion through a more tortuous pathway. Greater detail of the distal portion is shown in FIG. 2. Further explanation of these sections may be found in U.S. Pat. No. 5,534,007.

FIG. 3 shows the connection between the proximal shaft 7 and the midshaft 9, or optionally the distal shaft 12. The sections are preferably adhered together via an overlapping shaft sleeve 8 using a urethane bond or welded. The COBRAID™ guide wire inner shaft 10 (polyimide shaft with stainless steel braid from HVT Technologies), the pull back wire lumen 13 and the pull back wire can also be more easily seen.

FIG. 4 illustrates the problem that arises in prior conventional proximal shafts utilizing a guide wire shaft 10 and a free floating pull back wire 13a. The wire 13a tends to get twisted around the guide wire shaft 10 causing jumping and inaccurate stent placement. As mentioned above, these wires get tangled as the catheter is fed through the tortuous anatomy, such that when the pull back wire 13a is pulled via the sheath actuator 3 to retract the deployment sheath 17, the catheter recoils and binds up eventually surpassing the binding threshold, releasing the distal end of the catheter which lurches forward causing inaccurate placement of the stent. In testing prior art pull back stent delivery catheters which do not have a separate lumen in the proximal shaft, as shown in FIG. 4, the pull back wire tends to wind around the guide wire shaft. This creates a greater deployment force which causes jumping of the distal end of the catheter and recoil of the distal shaft as the physician pulls the pull back wire back. As the pull back wire tightens and the retaining means is abruptly released allowing the stent to be released, the distal end of the catheter jumps forward causing the stent to be deployed forward of the target site.

Figure 5:
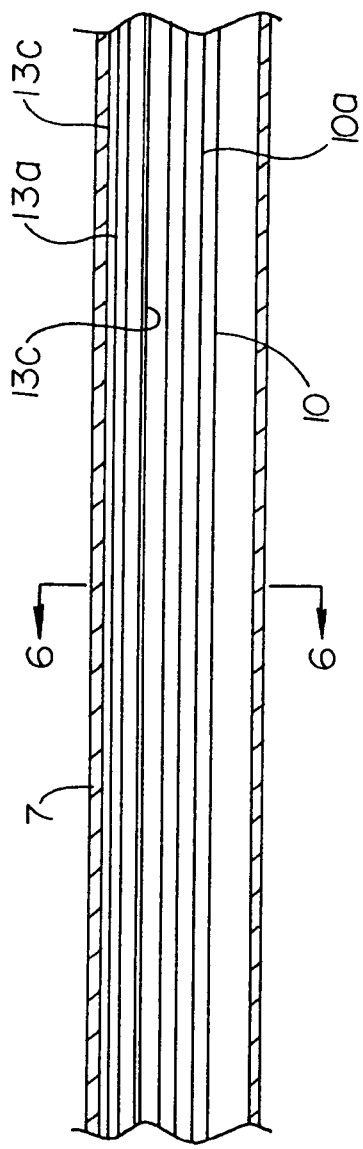
FIG. 5 shows a partial cross section of a proximal shaft of one embodiment of the invention.
Figure 6:
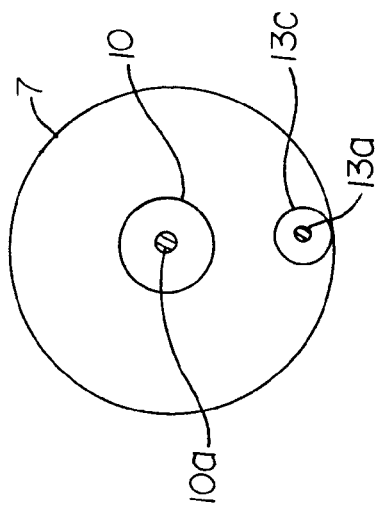
FIG. 6 is a transverse cross-section view of the shaft shown in FIG. 5 taken along the lines 6—6.

FIGS. 5 and 6 illustrate the first embodiment of the inventive proximal shaft 7. The shaft 7, which is typically made of COBRAID™, houses the guide wire shaft 10, preferably made of COBRAID™ or may be extruded plastic with the necessary lubrication for the guide wire, which houses the guide wire 10a. Also enclosed within the proximal shaft 7 is a pull back wire shaft 13c, preferably a hypotube, which is similar to a hypodermic needle and is made of stainless steel, but may be of other suitable material, such as polyethylene or a relatively thick plastic, which in turn houses the pull back wire 13a. The hypotube contributes stiffness allowing the proximal shaft 7 to be made of a more flexible material, such as polyethylene, especially when combined with a stiff guide wire shaft, such as COBRAID™. The pull back wire shaft 13c may be fastened to the inner wall of the proximal shaft or directly to the guide wire shaft 10. The pull back wire shaft 13c may also float freely without concern about entanglement because the pull back wire shaft is preferably coated with Teflon which allows the pull back wire to move easily and is prevented from wire to wire contact with the guide wire assembly which causes binding. A cross section of the this embodiment is shown in FIG. 6.

Figure 8:
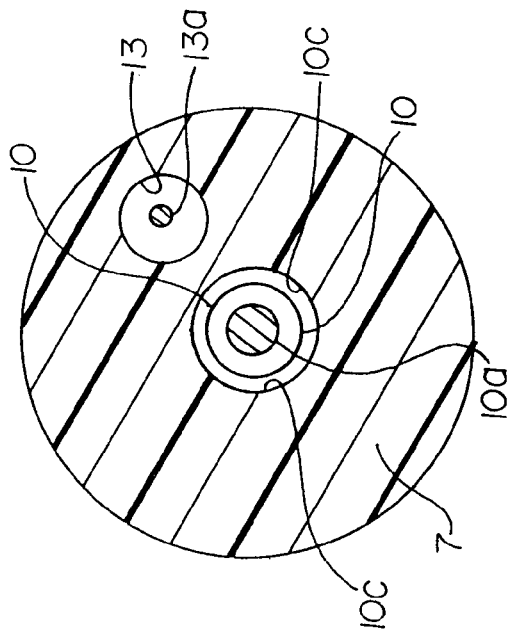
FIG. 8 is a transverse cross-section view of the shaft shown in FIG. 5 taken along the lines 8—8.
Figure 7:
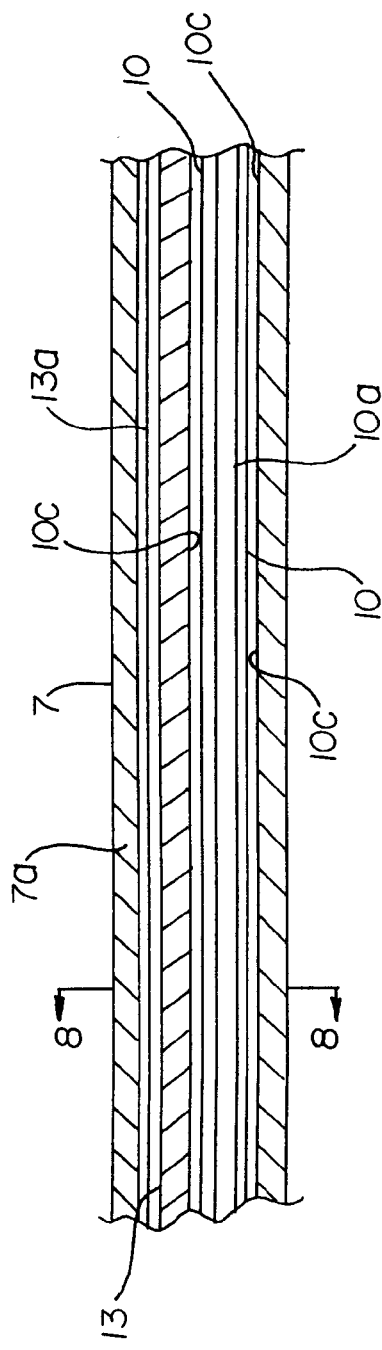
FIG. 7 shows a partial cross section of a proximal shaft of one embodiment of the invention.

FIGS. 7 and 8 illustrate a further embodiment of the proximal shaft 7, also seen in FIG. 3. In this embodiment the proximal shaft 7 is comprised of a single composite extrusion 7a having two lumens. Such material may be described as an extruded engineering thermoplastic polymeric material, preferably a linear aromatic polymer. Such materials include polyetherketone, polyketone, polyetherketoneketone, polyaryletherketone, polysulfone and polyether sulfone. Most preferably, polyetheretherketone (PEEK). As seen in FIG. 7, the shaft 7 is a solid piece having a guide wire lumen 10c, which preferably has a guide wire inner shaft 10 disposed therein, preferably a COBRAID shaft, and a pull back wire lumen 13. Since the shaft 7 is a single extrusion, the lumens 10c, and shaft 10, and lumen 13 never cross or get entangled, while maintaining the necessary stiffness. Both embodiments prevent entanglement and slack of the pull back wire 13a providing the user more precise control of the deployment sheath 17. A cross section of this embodiment is shown in FIG. 8.

It should be known that more lumens may be incorporated into the above embodiments to provide conduits for other purposes, i.e., a fluid lumen for an optional balloon.

The present proximal shaft exhibits stronger compression resistance and less flexibility then that of the distal portion of the delivery system. More flexible proximal shafts tend to create their own curvature and create tracking and deployment problems. The stiff proximal shaft having duel lumens/shafts improves push, trackability, stent deployment and eliminates slop and slack around turns by having separate lumens and keeping the wires separate.

The present invention also provides a system requiring a lower deployment force in releasing the loaded stent. That is, the pressure which the user must apply on the sheath actuator to retract the distal sheath and deploy the stent. The following test was done to demonstrate this improvement.

Deployment Force Test

The purpose of the test is to determine if a self expanding stent deployment system will deploy a stent in moderate tortuosity with a force on the retraction member 3 less than the minimum tensile specification. The deployment force is considered acceptable if when the stents are deployed, the forces required to deploy them are less than two pounds. Tests were done with an extruded double lumen polyetheretherketone (PEEK) proximal shaft with a COBRAID guide wire inner shaft and a conventional COBRAID™ proximal shaft with a COBRAID™ guide wire shaft and a free floating pull back wire.

Protocol 15 units were prepared for the test loaded with stents (size 20 mm×4.0 mm;
a minimum 10 lb/maximum 20 lb. Chatillon tensile tester on push/track tester; Teflon artificial arteries in 37° C. water bath, nominal size for the stents used with 1 inch radius section; and a 0.014 inch guidewire were provided;

Setup:
Submerge the artery test fixture in a 37° C. bath;
Slide the guide catheter through the connector on the side of the water bath and seat it in the artery model. Verify the guide is not placed in a compressed state.
Feed the guidewire down the guide catheter and across the 1" radius section of the artery.
Prep test units using saline solution.
Allow the devices to soak in the 37° C. water bath for a minimum of 0.25 hours before testing.

Procedure:
Back-load the delivery catheter over the guidewire and advance the delivery catheter down past the 1" radius section.

Illustration of Artificial Artery

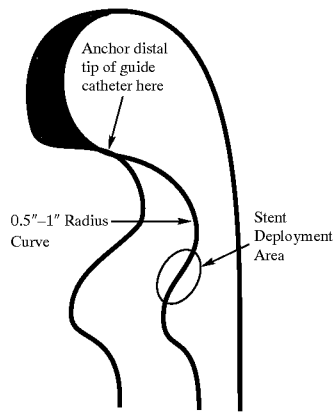

Center the bumper between the lines just past the curve. Pull back on the catheter to set final placement and remove any slack from the deployment catheter.

Note: Record how each unit is lined up before proceeding

Tighten Y-adapter touhy on catheter
Attach the luer to the Chatillon and assure there is no pre-load on the slider or the device.
Remove safety lock.
Set Chatillon to read the compression peak force and zero the Chatillon.
Hold Chatillon firmly on table. Be sure not to move the position of the stent.
Pull the slider back to deploy the stent. Do not touch any other part of the manifold. Note: Assure the slider does not bottom out against the luer.
Record the peak force that was required to deploy the stent.
Record the movement of the stent from the original location.

Results

| Sample | Results (lbs) |
| --- | --- |
| Deployment Force/Accuracy with OTW-20MM (Single shaft with floating pull back wire) | |
| 1 | 1.073 |
| 2 | 0.736 |
| 3 | 0.885 |
| 4 | 0.616 |
| 5 | 1.167 |
| 6 | 1.056 |
| 7 | 0.685 |
| 8 | 0.689 |
| 9 | 1.335 |
| 10 | 0.905 |
| 11 | 0.896 |
| 12 | 1.076 |
| 13 | 0.916 |
| 14 | 1.292 |
| 15 | 1.153 |
| Average | 0.965 |

-continued

Results

| Sample | Results (lbs) |
|---|---|
| Stdev | 0.223 |
| Max | 1.335 |
| Min | 0.616 |
| Deployment Force/Accuracy with OTW-20MM (with extruded double lumen PEEK Shaft) | |
| 1 | 0.33 |
| 2 | 0.27 |
| 3 | 0.32 |
| 4 | 0.23 |
| 5 | 0.35 |
| 6 | 0.38 |
| 7 | 0.41 |
| 8 | 0.29 |
| 9 | 0.39 |
| 10 | 0.41 |
| 11 | 0.32 |
| 12 | 0.34 |
| 13 | 0.43 |
| 14 | 0.37 |
| 15 | 0.29 |
| Average | 0.34 |
| Stdev | 0.06 |
| Max | 0.43 |
| Min | 0.23 |

As can be seen by the test results, the catheter incorporating the PEEK double lumen proximal shaft provided a much easier stent deployment with less pressure required. PEEK shafts were also more consistent as can be seen from the standard deviation allowing the physician more reliability in placement of the stent.

As mention above, a one-to-one force ratio in the proximal shaft is highly favorable for the users control in placement of the stent and prevents excessive jumping as the threshold of pushing past the lesion is compromised. The present invention supplies a comparable ratio at a much cheaper cost than that of the conventional proximal shaft. The following test is a force in, force out comparison of the proximal shafts of the present invention and a conventional proximal shaft. Three shafts were tested: 1) a PEEK extruded double lumen proximal shaft; 2) a PEEK extruded double lumen proximal shaft with an inner COBRAID™ guide wire shaft; and 3) a COBRAID™ proximal shaft having a COBRAID guide wire shaft. The PEEK extruded shafts are much cheaper to make than the conventional COBRAID shaft. Force was applied to the proximal end and pushed 0.01, 0.02 and 0.03 inches, consecutively. The force exerted at the distal end was measured for all three distances. The forces from the proximal end and the respective distal ends were compared. The optimum result is a one-to-one force ratio. Three trial runs were done for each sample.

Extruded PEEK Double Lumen

| Trial Run | Distance pushed in (inches | Force In (grams) | Force Out (grams) | Difference |
|---|---|---|---|---|
| 1 | 0.01 | 42.4 | 35 | 7.4 |
| 1 | 0.02 | 84 | 70 | 14 |
| 1 | 0.03 | 126.6 | 104 | 22.6 |

-continued

Extruded PEEK Double Lumen

| Trial Run | Distance pushed in (inches | Force In (grams) | Force Out (grams) | Difference |
|---|---|---|---|---|
| 2 | 0.01 | 41.6 | 35 | 6.6 |
| 2 | 0.02 | 82.4 | 70 | 12.4 |
| 2 | 0.03 | 122.2 | 102 | 20.2 |
| 3 | 0.01 | 41.6 | 34 | 7.6 |
| 3 | 0.02 | 82 | 70 | 12 |
| 3 | 0.03 | 125.4 | 104 | 21.4 |
| average 1 | | 41.87 | 34.67 | 7.2 |
| average 2 | | 82 | 70 | 12.80 |
| average 3 | | 125.4 | 103.33 | 21.40 |

Extruded PEEK Double Lumen With COBRAID ™ Guide Wire Shaft

| Trial Run | Distance pushed in (inches | Force In (grams) | Force Out (grams) | Difference |
|---|---|---|---|---|
| 1 | 0.01 | 43.2 | 36 | 7.2 |
| 1 | 0.02 | 86.6 | 72 | 14.6 |
| 1 | 0.03 | 158 | 106 | 52 |
| 2 | 0.01 | 42.4 | 25 | 17.4 |
| 2 | 0.02 | 86.4 | 72 | 14.4 |
| 2 | 0.03 | 152.4 | 106 | 46.4 |
| 3 | 0.01 | 41.2 | 37 | 4.2 |
| 3 | 0.02 | 86 | 72 | 14 |
| 3 | 0.03 | 149.2 | 106 | 43.2 |
| average 1 | | 42.27 | 32.67 | 9.60 |
| average 2 | | 86.33 | 72 | 14.33 |
| average 3 | | 153.20 | 106 | 47.2 |

COBRAID ™ Shaft with Cobraid Guide Wire Shaft

| Trial Run | Distance pushed in (inches | Force In (grams) | Force Out (grams) | Difference |
|---|---|---|---|---|
| 1 | 0.01 | 43 | 37 | 6 |
| 1 | 0.02 | 84.4 | 73 | 11.4 |
| 1 | 0.03 | 150 | 106 | 44 |
| 2 | 0.01 | 43.4 | 36 | 7.4 |
| 2 | 0.02 | 83.8 | 72 | 11.8 |
| 2 | 0.03 | 146.6 | 106 | 40.6 |
| 3 | 0.01 | 42 | 36 | 6 |
| 3 | 0.02 | 83.2 | 72 | 11.2 |
| 3 | 0.03 | 146.2 | 106 | 40.2 |
| average 1 | | 42.8 | 36.33 | 6.47 |
| average 2 | | 83.8 | 72.33 | 11.47 |
| average 3 | | 147.60 | 106 | 41.6 |

As can be seen, the present invention provides comparable results to the more expensive COBRAID™ shaft at a much cheaper cost.

While this invention may be embodied in many different forms, there are described in detail herein specific preferred embodiments of the invention. This description is an exemplification of the principles of the invention and is not intended to limit the invention to the particular embodiments illustrated.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A medical catheter comprising:

a proximal catheter shaft forming a lumen having a proximal end and a distal end, the proximal shaft having at least two inner shafts disposed within the proximal shaft, the at least two inner shafts each forming a separate and unshared lumen relative to each other;

a distal catheter shaft being more flexible than the proximal catheter shaft, having a proximal end and a distal end, wherein the distal end of the proximal shaft is connected to the proximal end of the distal shaft;

a manifold connected to the proximal end of the proximal shaft;

a stent loaded on the distal end of the catheter, the stent having an expanded state and a collapsed state;

a stent retaining means situated at the distal end of the catheter retaining the stent in its collapsed state; and a retracting means communicating with the retaining means and extending from the retaining means through one of the at least two shafts within the proximal shaft to the manifold.

2. The medical device of claim 1, wherein one of the at least two shafts is a guide wire shaft and wherein the guide wire shaft comprises a polymer composite with a metal braided tube.

3. The medical device of claim 2, further comprising a guide wire which extends from the manifold through the guide wire shaft within the proximal shaft and the distal shaft to the distal end of the distal shaft.

4. The medical device of claim 3, wherein the retaining means is a deployment sheath and the retracting means is a pull back wire, wherein one of the at least two shafts is a pull back wire shaft and the pull back wire is disposed therein, the distal end of the pull back wire being connected to the deployment sheath and the proximal end of the pull back wire communicating with the manifold, such that the pull back wire may be pulled proximally, retracting the deployment sheath and releasing the stent.

5. The medical device of claim 4, wherein the pull back wire shaft and a guide wire shaft are both disposed within the proximal shaft extending from the proximal end to the distal end of the proximal shaft.

6. The medical device of claim 5, wherein the pull back shaft is a hypotube.

7. The medical device of claim 6, wherein the polymer composite with a metal braided tube is a polyimide polymer conformingly encasing a braided tube of stainless steel ribbon.

8. The medical device of claim 6, wherein the proximal shaft comprises a polyimide shaft with a steel braid encased therein.

9. The medical device of claim 7, wherein the proximal shaft comprises a polyimide shaft with a steel braid encased therein.

10. A medical catheter comprising:

a proximal catheter shaft having a proximal end and a distal end, the proximal shaft having at least two inner lumens disposed within the proximal shaft;

a distal catheter shaft being more flexible than the proximal catheter shaft, having a proximal end and a distal end, wherein the distal end of the proximal shaft is connected to the proximal end of the distal shaft;

a manifold connected to the proximal end of the proximal shaft;

a stent loaded on the distal end of the catheter, the stent having an expanded state and a collapsed state;

a stent retaining means situated at the distal end of the catheter retaining the stent in its collapsed state; and a retracting means communicating with the retaining means and extending from the retaining means through one of the at least two lumens within the proximal shaft to the manifold.

11. The medical device of claim 10, wherein one of the at least two inner lumens is a guide wire lumen, the guide wire lumen including an inner guide wire shaft disposed within the guide wire lumen of the proximal shaft, and wherein the guide wire shaft comprises a polymer composite with a metal braided tube.

12. The medical device of claim 11, further comprising a guide wire which extends from the manifold through the guide wire lumen within the proximal shaft and the distal shaft to the distal end of the distal shaft.

13. The medical device of claim 12, wherein the retaining means is a deployment sheath and the retracting means is a pull back wire, wherein one of the at least two lumen is a pull back wire lumen and the pull back wire is disposed therein, the distal end of the pull back wire being connected to the deployment sheath and the proximal end of the pull back wire communicating with the manifold, such that the pull back wire may be pulled proximally, retracting the deployment sheath and releasing the stent.

14. The medical device of claim 13, wherein the proximal shaft is formed at least in part of an extruded engineering thermoplastic polymeric material.

15. The medical device of claim 14, wherein the polymeric material is a linear aromatic polymer.

16. The medical device of claim 15, wherein the linear aromatic polymer is selected from the group consisting of polyetheretherketone, polyetherketone, polyketone, polyetherketoneketone, polyaryletherketone, polysulfone and polyether sulfone.

17. The medical device of claim 14, wherein the extruded polymeric material is polyetheretherketone, the proximal shaft having two lumens therein extending from the proximal end to the distal end of the proximal shaft.

18. The medical device of claim 17, wherein the pull back wire is disposed within the pull back lumen and the guide wire is disposed within the the inner guide wire shaft.

19. The medical device of claim 18, wherein the inner guide wire shaft includes disposed therein a polyimide shaft with a steel braid encased therein.

20. The medical catheter of claim 1, the proximal catheter shaft having a profile and the distal catheter shaft having a profile, wherein the profile of the proximal shaft and the profile of the distal shaft are substantially the same along a majority of their length.

21. The medical device of claim 20, wherein one of the at least two shafts is a guide wire shaft and wherein the guide wire shaft comprises a polymer composite with a metal braided tube.

22. The medical catheter of claim 10, the proximal catheter shaft having a profile and the distal catheter shaft having a profile, wherein the profile of the proximal shaft and the profile of the distal shaft are substantially the same along a majority of their length.

23. The medical device of claim 22, wherein one of the at least two inner lumens is a guide wire lumen, the guide wire lumen including an inner guide wire shaft disposed within the guide wire lumen of the proximal shaft, and wherein the guide wire shaft comprises a polymer composite with a metal braided tube.

24. A medical catheter comprising:

a proximal catheter shaft forming a lumen having a proximal end and a distal end, the proximal shaft having at least two inner shafts disposed within the lumen of the proximal shaft, the at least two inner shafts each forming a distinct passageway within the lumen of the proximal shaft;

a distal catheter shaft being more flexible than the proximal catheter shaft, having a proximal end and a distal end, wherein the distal end of the proximal shaft is connected to the proximal end of the distal shaft;

a manifold connected to the proximal end of the proximal shaft;

a stent loaded on the distal end of the catheter, the stent having an expanded state and a collapsed state;

a stent retaining means situated at the distal end of the catheter retaining the stent in its collapsed state; and a retracting means communicating with the retaining means and extending from the retaining means through one of the at least two shafts within the proximal shaft to the manifold.

* * * * *